(12) United States Patent
Knox (10) Patent No.: US 10,918,345 B2
(45) Date of Patent: Feb. 16, 2021

(54) ASSEMBLY FOR A COMPUTER TOMOGRAPHY (CT) SYSTEM AND RELATED METHOD

(71) Applicant: Analogic Corporation, Peabody, MA (US)

(72) Inventor: Jeffrey Knox, Lynnfield, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 16/507,555

(22) Filed: Jul. 10, 2019

(65) Prior Publication Data

US 2021/0007681 A1    Jan. 14, 2021

(51) Int. Cl.
*A61B 6/03* (2006.01)
*F16C 13/04* (2006.01)
*F16C 32/06* (2006.01)
*A61B 6/00* (2006.01)

(52) U.S. Cl.
CPC .............. *A61B 6/035* (2013.01); *A61B 6/44* (2013.01); *A61B 6/4435* (2013.01); *F16C 13/04* (2013.01); *F16C 32/0618* (2013.01); *A61B 6/56* (2013.01)

(58) Field of Classification Search
None
See application file for complete search history.

(56) References Cited

U.S. PATENT DOCUMENTS

| | | | | |
|---|---|---|---|---|
| 4,912,735 A * | 3/1990 | Beer | ...................... | A61B 6/035 378/15 |
| 6,276,145 B1 * | 8/2001 | Sharpless | ................ | A61B 6/035 378/15 |
| 7,477,721 B2 * | 1/2009 | Chappo | ................... | A61B 6/032 378/13 |
| 7,957,786 B2 * | 6/2011 | Katcha | ................ | G01R 33/3692 600/407 |
| 8,270,563 B2 * | 9/2012 | Harris | .................... | F16C 19/502 378/15 |
| 8,299,670 B2 * | 10/2012 | Krumme | ............. | F16C 32/0696 310/90 |
| 8,526,571 B2 * | 9/2013 | Pettinato | ............. | F16C 32/0666 378/4 |
| 8,796,893 B2 * | 8/2014 | Muth | ................... | F16C 32/0666 310/90 |
| 8,817,945 B2 * | 8/2014 | Pettinato | ............. | F16C 32/0666 378/15 |

(Continued)

*Primary Examiner* — Thomas R Artman
(74) *Attorney, Agent, or Firm* — TraskBritt (57) ABSTRACT

An assembly for a system includes a rotatable drum defining a bore and configured for rotation about an object positioned within the bore, a support structure configured to support the rotatable drum during a rotation of the drum, a first radial air bearing disposed between the rotatable drum and the support structure and positioned proximate to a first distal end of the rotatable drum, and a second radial air bearing disposed between the rotatable drum and the support structure and positioned proximate to a second, opposite distal end of the rotatable drum. The first radial air bearing and the second radial air bearing are located at different longitudinal positions along a longitudinal axis of the rotatable drum and the first radial air bearing and the second radial air bearing are configured to levitate the rotatable drum relative to the support structure.

27 Claims, 11 Drawing Sheets

(56) References Cited

U.S. PATENT DOCUMENTS

| | | | | |
|---|---|---|---|---|
| 8,899,833 B2* | 12/2014 | Sharpless | ................ | A61B 6/035 |
| | | | | 378/197 |
| 9,011,001 B2* | 4/2015 | Sahin Nomaler | ...... | H02K 41/03 |
| | | | | 378/197 |
| 9,538,963 B2* | 1/2017 | Smithanik | ............... | A61B 6/035 |
| 10,182,777 B2* | 1/2019 | Murch | .................... | A61B 6/56 |
| 2007/0230654 A1* | 10/2007 | Chappo | ................. | A61B 6/035 |
| | | | | 378/15 |
| 2010/0034492 A1* | 2/2010 | Krumme | ................ | A61B 6/035 |
| | | | | 384/107 |
| 2010/0254640 A1* | 10/2010 | Muth | ..................... | A61B 6/035 |
| | | | | 384/107 |
| 2011/0062354 A1* | 3/2011 | Pettinato | .................. | H05G 1/26 |
| | | | | 250/522.1 |
| 2011/0158382 A1* | 6/2011 | Sahin Nomaler | ... | F16C 32/0461 |
| | | | | 378/21 |
| 2011/0194669 A1* | 8/2011 | Tremaine | .............. | F16C 19/502 |
| | | | | 378/15 |
| 2012/0027183 A1* | 2/2012 | Sharpless | .............. | F16C 19/163 |
| | | | | 378/197 |
| 2013/0308759 A1* | 11/2013 | Pettinato | ............. | F16C 32/0666 |
| | | | | 378/207 |
| 2014/0270051 A1* | 9/2014 | Smithanik | ........... | F16C 32/0485 |
| | | | | 378/4 |
| 2017/0238889 A1* | 8/2017 | Murch | ................... | A61B 6/035 |
| 2017/0321749 A1* | 11/2017 | Tremaine | ............ | F16C 32/0446 |

* cited by examiner

ASSEMBLY FOR A COMPUTER TOMOGRAPHY (CT) SYSTEM AND RELATED METHOD

TECHNICAL FIELD

The present application relates to the field of computer tomography (CT) imaging and, in particular, to the levitation of a rotatable gantry during operation.

BACKGROUND

In a conventional CT imaging system, a rotatable gantry physically contacts various components of the CT imaging system. For example, a motor drives the rotation of gantry by physical linkage (e.g., belt, chain, etc.). Additionally, the conventional CT imaging system includes mechanical bearings coupled to a stationary cradle. The bearings reduce friction between the rotating gantry and the cradle. However, the friction generated by the rotation of the linkage and the bearing creates wear and tear on the linkage and the bearings. This in turn, requires undesired maintenance and/or replacement of the linkage and bearings.

BRIEF DESCRIPTION OF THE DRAWINGS

The application is illustrated by way of example and is not limited by the accompanying drawings, in which like references generally indicate similar elements and in which.

DETAILED DESCRIPTION

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a contactless rotatable gantry (or rotatable drum) in a computed tomography (CT) imaging system. In conventional systems, a rotatable gantry physically contacts one or more components (e.g., motor, chain drive, belt drive, bearing, etc.) during operation. The friction of the physical contact of components during rotation of the gantry causes undesired wear and tear on the CT imaging system. In various embodiments described herein, a CT imaging system includes air bearings that provide an air gap between respective air bearings and a rotatable gantry during operation. As such, a rotatable gantry may levitate while rotating during operation. Levitation of a rotatable gantry eliminates friction between the rotatable gantry and proximate components. As a result, less energy may be required to rotate a gantry and a life-span of a gantry and other components of the CT imaging system may be increased as compared to CT imaging systems that use mechanical bearings or otherwise experience some physical contact between rotating and stationary parts. Moreover, air bearings create a constant air gap between the air bearings and a gantry which improves axial alignment of the gantry. This causes reduced (or eliminated) wobble/jitter of a gantry during rotation as compared to CT imaging systems that do not use bearing for axial alignment, and less friction as compared to CT imaging systems that use mechanical bearings for axial alignment.

In various embodiments described herein, a CT imaging system includes an inductive motor that contactlessly rotates a rotatable gantry. The inductive motor may include a rotor portion and a stator portion. As will be described in further detail below, changes of a magnetic field of a stator portion causes contactless rotation of a rotor portion. Thus, in various embodiments, an inductive motor causes contactless rotation of a gantry.

Additionally, in various embodiments described herein, the CT imaging system includes a contactless communication system. For example, at least one of the members of the communication system is movable (e.g., rotatable) relative to the other member and the two members are separated by an air gap. The communication system is at least comprised of a contactless data-link (e.g., comprising at least two antennas or other mediums for the transmission of information) and a transceiver configured to send and/or receive information signals indicative of information to be transferred between the first member and the second member via the contactless data-link.

It may be appreciated that "noncontact," "contactless," and/or the like is used herein to refer to an airgap (or fluid gap) between a rotatable gantry and one or more stationary components of the CT scanning system. Also, during rotation of a rotatable gantry, information may be transmitted to and from the rotatable gantry without physical contact of transmission/receiving components. It should also be appreciated that "noncontact," "contactless," and/or the like should not be understood to necessarily preclude possible contact between or among such bodies for other purposes, including, for example, electrostatic discharge, braking and safety mechanisms, etc. It may also be appreciated that in the present disclosure, except where otherwise clear from context, "gap" and "air gap" and/or the like are used more or less interchangeably, and are not intended to be limited to air, it being possible for vacuum, oil, and/or other fluid and/or gas permitting relative movement to completely or partially fill such gaps or spaces.

Figure 1:
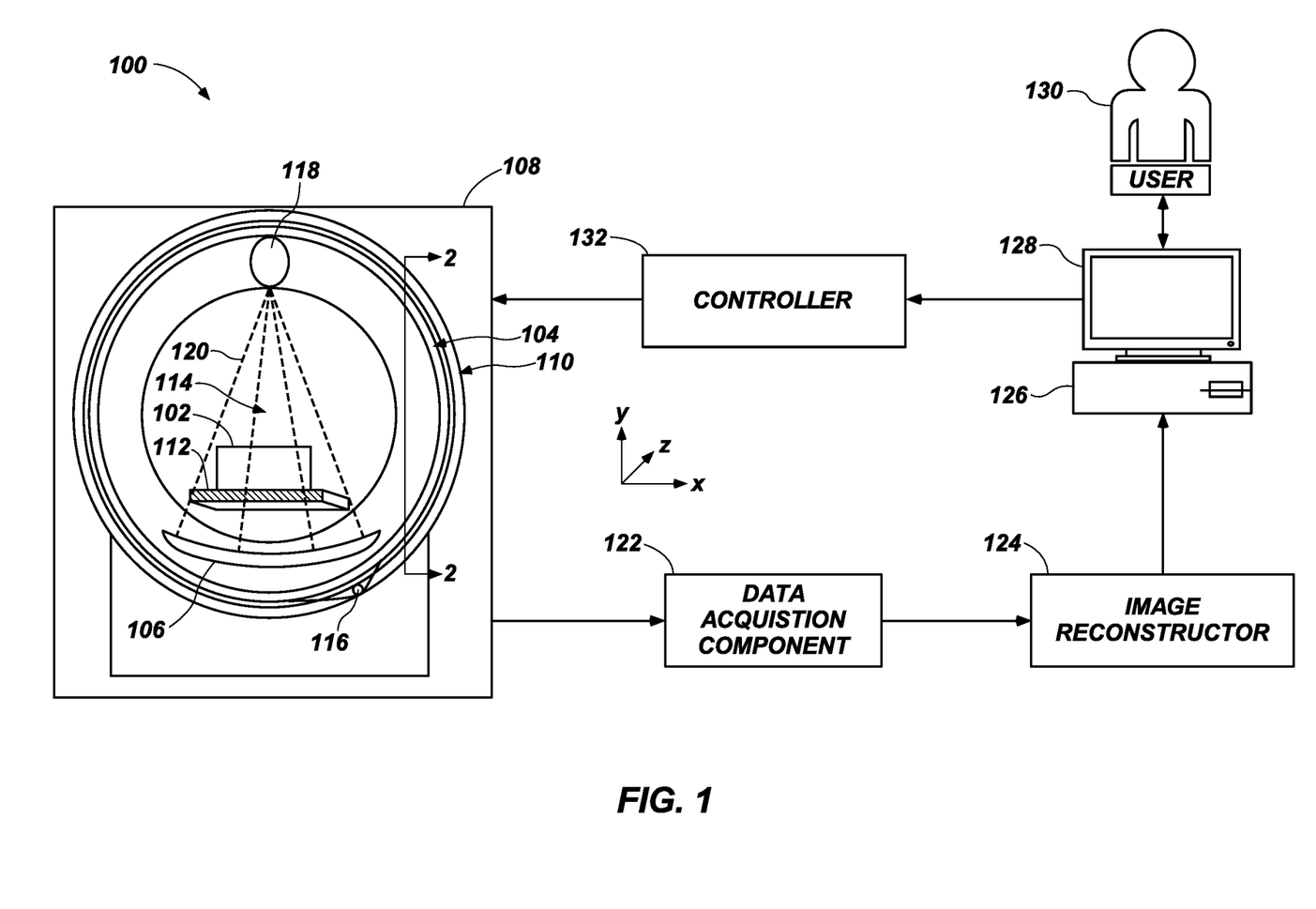
FIG. 1 illustrates an example CT scanning environment.

FIG. 1 illustrates environment 100 of a contactless CT imaging system. More particularly, FIG. 1 illustrates an example CT imaging modality that may be configured to acquire volumetric information regarding object 102 under examination and generate images therefrom. It may be appreciated that environment 100 is merely an example and is not intended to be interpreted in a limiting manner, such as necessarily specifying the location, inclusion, and/or relative arrangement of the components depicted therein.

For example, a data acquisition component 122 as illustrated in FIG. 1 may be part of rotating member 104 of object examination apparatus 108, or more particularly may be part of detector array 106, for example.

In environment 100, object examination apparatus 108 is configured to examine one or more objects 102 (e.g., a series of suitcases at an airport, a human patient, etc.). Object examination apparatus 108 may comprise rotating member 104 (also referred to as a rotatable gantry or rotatable drum) and stationary member 110. During an examination of object(s) 102, object(s) 102 may be placed on support article 112, such as a bed or conveyor belt, that is selectively positioned in examination region 114 (e.g., a hollow bore in rotating member 104), and rotating member 104 may be rotated about object(s) 102 by rotator 116 (e.g., motor).

Rotating member 104 may surround a portion of examination region 114 and may comprise one or more radiation sources 118 (e.g., an x-ray source, gamma-ray source, or other ionizing radiation source) and detector array 106 that is mounted on a substantially diametrically opposite side of rotating member 104 relative to radiation source(s) 118. During an examination of object(s) 102, radiation source(s) 118 emits fan, cone, wedge, and/or other shaped radiation 120 configurations into examination region 114 of object examination apparatus 108. It may be appreciated that such radiation may be emitted substantially continuously and/or may be emitted intermittently (e.g., a short pulse of radiation is emitted followed by a resting period during which radiation source(s) 118 is not activated).

As emitted radiation 120 traverses object(s) 102, radiation 120 may be attenuated differently by different aspects of object(s) 102. Because different aspects attenuate different percentages of radiation 120, an image(s) may be generated based upon the attenuation, or variations in the number of radiation photons that are detected by detector array 106. For example, more dense aspects of object(s) 102, such as a bone or metal plate, may attenuate more of radiation 120 (e.g., causing fewer photons to be detected by detector array 106) than less dense aspects, such as skin or clothing.

Detector array 106 is configured to directly convert (e.g., using amorphous selenium and/or other direct conversion materials) and/or indirectly convert (e.g., using a scintillator(s) and photo-detectors and/or other indirect conversion materials) detected radiation into signals that may be transmitted from detector array 106 to data acquisition component 122 (e.g., typically positioned on rotating member 104) configured to convert analog signals output by detector array 106 into digital signals and/or to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that were emitted while radiation source 118 was at a particular angular range relative to object 102. Based upon the compiled signals, data acquisition component 122 may generate projection data indicative of the compiled signals, for example.

Information may be transmitted between components physically attached to rotating member 104 (e.g., such as detector array 106 and/or data acquisition component 122) and components that are not physically attached to rotating member 104 (e.g., such as image reconstructor 124) through a contactless data-link. By way of example, the projection space data generated by data acquisition component 122 may be transmitted via a communication system to image reconstructor 124 positioned on the stationary side of the imaging modality. As may be described in more detail below, such a communication system may comprise, among other things, a first transceiver (e.g., mounted to rotating member 104), a contactless data-link (e.g., comprising a first antenna mounted to rotating member 104 and a second antenna mounted to stationary member 110), and a second transceiver (e.g., mounted to stationary member 110). In this way, information may be transferred between rotating member 104 and stationary member 110. Additional description regarding information transferred between rotating member 104 (e.g., rotor) and stationary member 110 (e.g., stator) will be provided in further detail below.

Figure 2A:
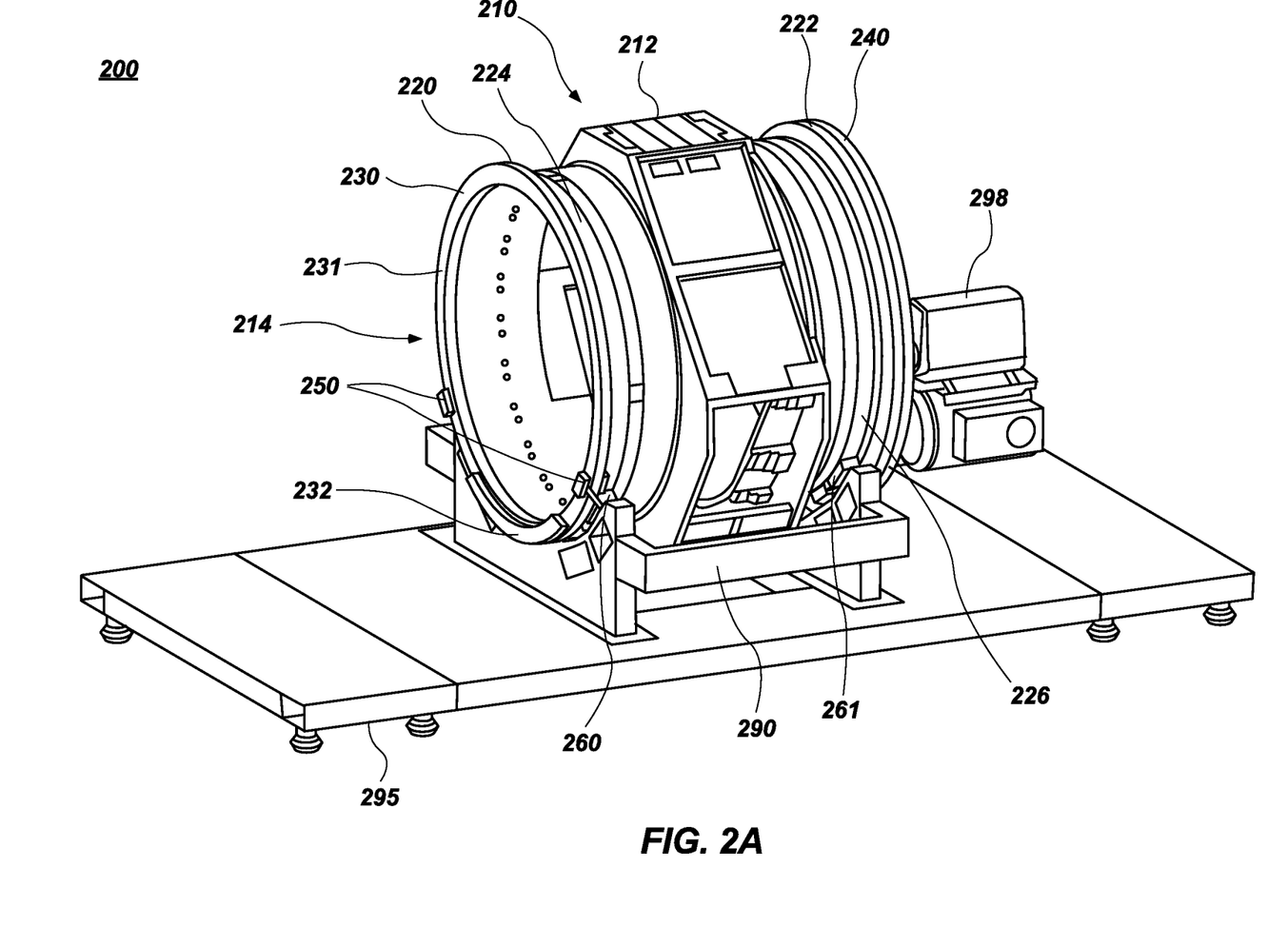
FIG. 2A is a perspective view of a CT scanning system to some embodiments.
Figure 2B:
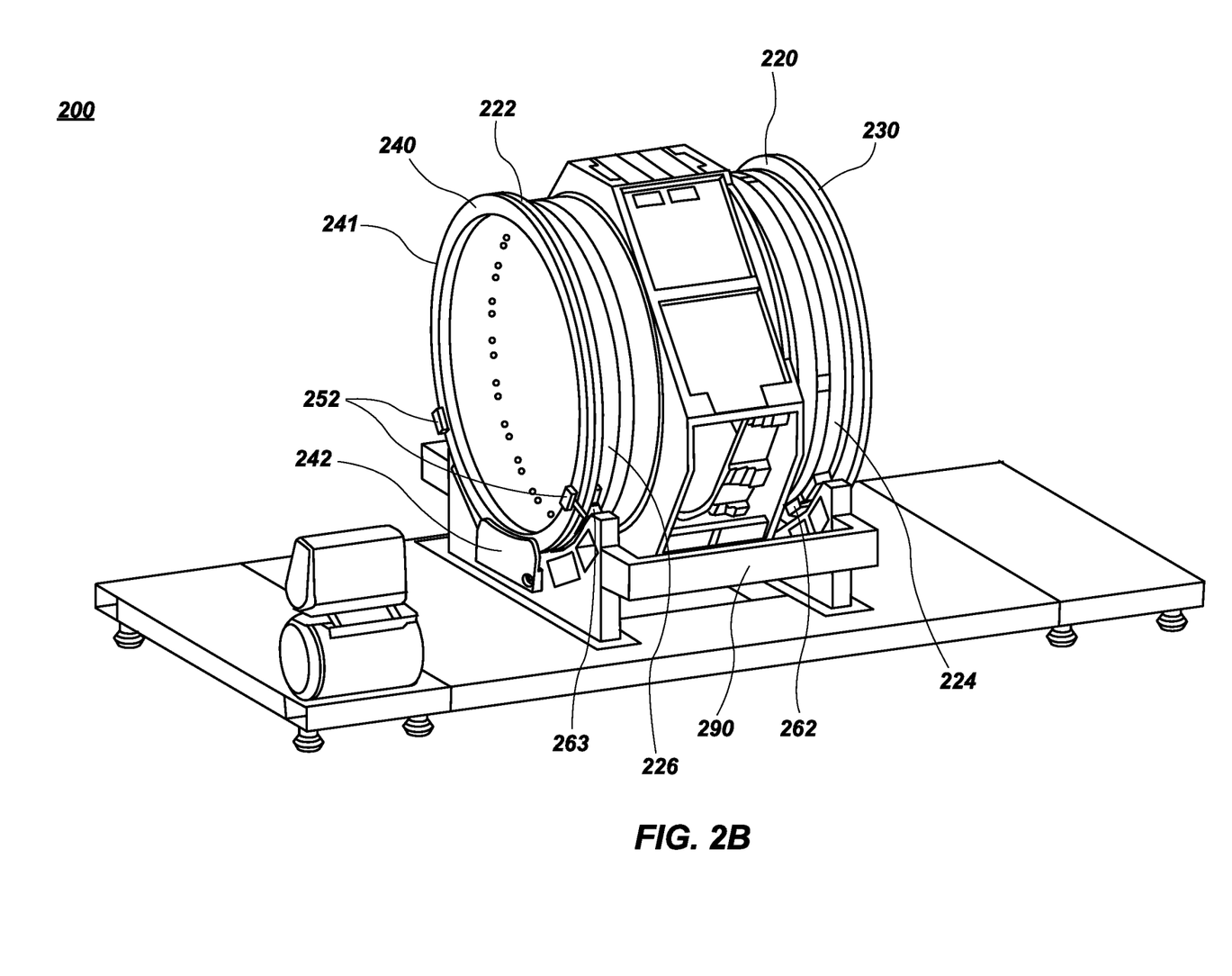
FIG. 2B is a perspective view of a CT scanning system to some embodiments.

FIGS. 2A and 2B illustrate an embodiment of CT scanning system 200.

FIG. 2A illustrates a first isometric view of CT scanning system 200 and FIG. 2B depicts a second (and opposite) isometric view of system 200. CT scanning system 200 includes rotatable drum 210 (also referred to as a rotatable gantry). Drum 210, in various embodiments, is similar to rotating member 104 as described with respect to FIG. 1. For example, drum 210 includes radiation source 212 (e.g., similar to radiation source 118) that emits fan, cone, wedge, and/or other shaped radiation configurations into the examination region 214. The emitted radiation is to examine an object (not shown) placed in examination region 214. CT scanning system 200 includes cradle 290 for cradling drum 210. Cradle 290 is mounted on base 295.

During a contemplated operation of the CT scanning system 200, rotatable drum 210 contactlessly rotates with respect to cradle 290. That is, rotatable drum 210 rotates with respect to cradle 290 free of physical contact with cradle 290 or any other component (e.g., motor, information receiver/transmitter components, etc.). It should be appreciated that, in various embodiments, rotatable drum 210 makes contact with radial air bearings when CT scanning system 200 is not in operation (e.g., when rotatable drum 210 is not rotating and an air gap is not formed between rotatable drum and the radial air bearings).

CT scanning system 200 includes air bearings (also called aerostatic air bearings or aerodynamic bearings) disposed between cradle 290 and rotatable drum 210. In disclosed embodiments, air bearings generate an air gap between rotatable drum 210 and the respective air bearing which enables drum 210 to contactlessly rotate. As depicted in FIGS. 2A and 2B, system 200 includes radial air bearings 260 and 261 (see FIG. 2A) and radial air bearings 263 and 264 (see FIG. 2B) that radially support drum 210 by providing an air gap along the radial surface of drum 210. Radial air bearings 260 are disposed on first side of cradle 290 and radial air bearings 262 are disposed on a second opposite side of cradle 290. Similarly, radial air bearings 261 are disposed on the first side of cradle 290 and radial air bearings 263 are disposed on a second opposite side of cradle 290.

In various embodiments, cradle 290 circumferentially surrounds drum 210. In such an embodiment, the air bearings (e.g., radial and/or axial air bearings) are spaced apart around the circumference of the drum.

Referring to FIG. 2A, radial air bearings 260 and 261 are spaced apart longitudinally from one another. For example, radial air bearings 260 are disposed proximate a first distal end of drum 210 and radial air bearings 261 are disposed proximate a second opposite distal end of drum 210. Similarly, radial air bearings 262 and 263 are spaced apart longitudinally from one another.

As depicted in FIGS. 2A and 2B, radial air bearings 260-263 each include two separate air bearings. In various embodiments, radial air bearings 260-263 may each include a single radial air bearing. In various embodiments, radial air bearings 260-263 may each include two or more radial air bearings that are aligned along respective radial surfaces 224 and 226.

While pressurized gas (e.g., air) is supplied to radial air bearings 260 and 263, an air gap exists along radial surface 224 of drum 210, and while pressurized gas is supplied to radial air bearing 262 and 264, an air gap exists along radial surface 226 of drum 210. The radial air bearings maintain a constant air gap between the respective radial air bearing and the radial surface of the rotatable drum (e.g., radial surfaces 224 and 226). The constant air gap eliminates any friction between the air bearings during rotation. Moreover, the constant air gap creates a constant bearing surface between the drum and the air bearings which reduces or eliminates wobble/jitter of the drum during rotation. Radial surfaces 224 and 226, in various embodiments, are polished surfaces.

CT scanning system 200 includes axial air bearing 250 disposed proximate a first end of drum 210 and axial air bearings 252 disposed at a second opposite end of drum 210. The axial air bearings axially align drum 210 with respect to cradle 290 during operation. As will be described in further detail below, CT scanning system 200, in various embodiments, includes one or more of an induction motor and an information transmission system both of which generate an axial force on the drum. In some embodiments, the induction motor and the information transmission system are disposed on opposite ends of drum 210 and each cause axial forces on the drum. The axial forces may be opposing each other or in the same direction. Other factors may generate an axial force on the drum. For example, CT scanning system 200 may not be level which may cause CT scanning system 200 to be axially unaligned.

The axial air bearings generate a constant air gap that opposes the externally generated axial forces as described above. As a result, drum 210 remains axially aligned with respect to cradle 290 during operation. In one embodiment, the force generated by the axial air bearings oppose one another. For example, axial air bearings 250 (at a first distal end of drum 210) generate a force in a first direction (e.g., in the direction of surface 231) and axial air bearings 252 (at a second opposite distal end of drum 210) generate a force in a second opposite direction (e.g., in the direction of surface 241).

The constant air gap eliminates any friction between the air bearings during rotation. Moreover, the constant air gap creates a constant bearing surface between the air bearings and drum which reduces or eliminates wobble/jitter of the drum during rotation. As will be described in further detail below, the axial air bearings are proximate a single flange or respective annular flanges. As such, the axial air bearings create an air gap with a single flange or respective annular flanges.

Referring to FIGS. 2A and 2B, drum 210 includes a first annular flange 220 proximate a first distal end of drum 210 and a second annular flange 222 disposed proximate a second opposite distal end of drum 210. Flanges 220 and 222 each protrude radially from the outer surface of the drum.

Rotor 230 (e.g., ring) of the information transmission system is proximate (e.g., coupled to) flange 220. As such, axial air bearings 250 create an air gap between annular surface 231 and the axial air bearings. Stator 232 of the information transmission system is proximate rotor 230. Additionally, an air gap (generated, at least in part, by axial air bearings) is between rotor 230 and stator 232.

In one embodiment, rotor 230 is embedded in flange 220. That is, the combination of the rotor and flange 220 are a single flange. As such, axial air bearings 250 create an air gap between the axial air bearings and the flange (e.g., combination of the rotor and flange 220). In another embodiment, annular flange 220 is the rotor of the information system. In such an embodiment, axial air bearings 250 create an air gap between annular flange 220 and the axial air bearings.

Rotor 240 (e.g., ring) of the induction motor is proximate (e.g., coupled to) flange 222. As such, axial air bearings 252 create an air gap between annular surface 241 of rotor 240. In one embodiment, rotor 240 is embedded in flange 222. That is, the combination of the rotor and flange 222 are a single flange. As such, axial air bearings 252 create an air gap between the axial air bearings and the flange (e.g., combination of the rotor and flange 222). In another embodiment, annular flange 222 is the rotor of the induction motor. In such an embodiment, axial air bearings 252 create an air gap between annular flange 222 and the axial air bearings. Stator 242 of the induction motor is proximate rotor 240. In various embodiments, axial air bearings are arranged in such a manner as to oppose the magnetic attraction of the both the (1) motor stator and rotor, and (2) information transmission stator. Additionally, the axial air bearings do not allow pitch, yaw and roll due to the attractive forces at either rotor or stator inductive coupling.

Figure 3:
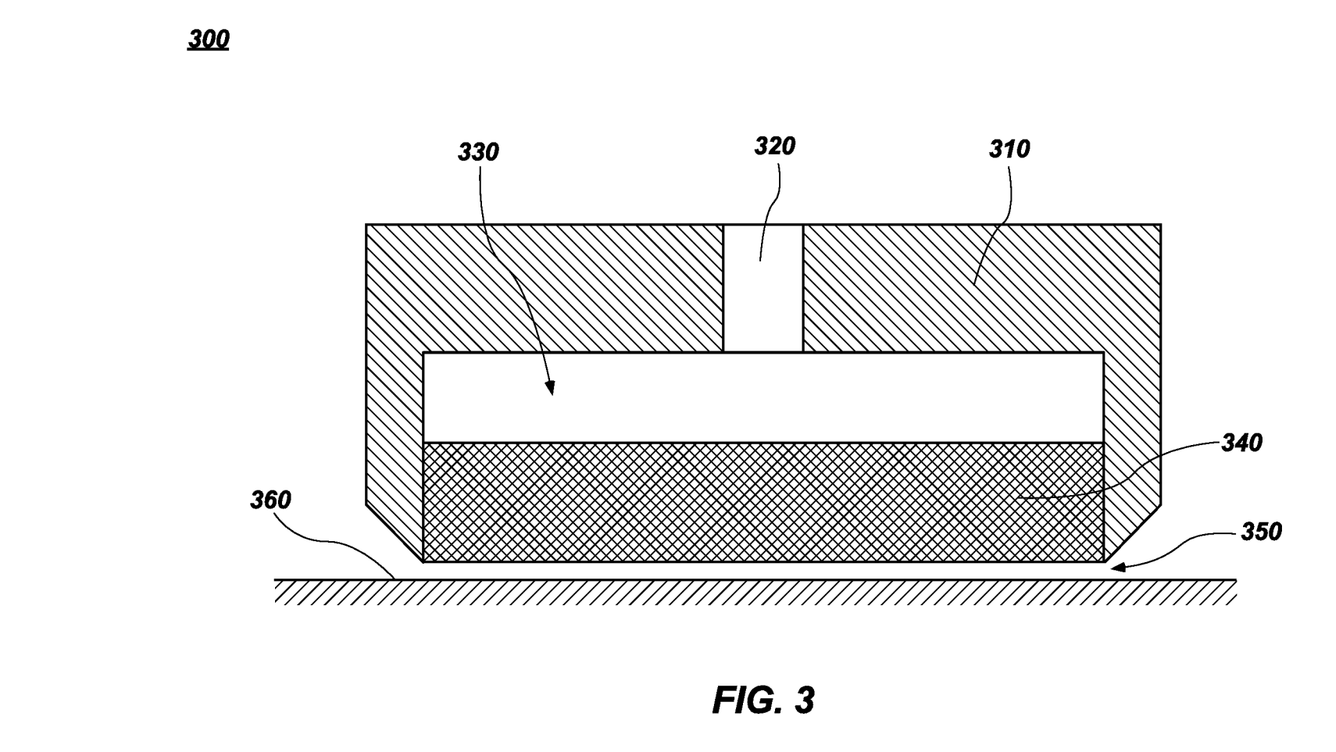
FIG. 3 is a cross-sectional view of an air bearing according to some embodiments.

FIG. 3 is a cross-sectional view of an embodiment of an air bearing 300. Air bearing 300 is an example of an axial air bearing. Additionally, air bearing 300 is an example of a radial air bearing. However, a radial air bearing is curved to accommodate the radial curvature of the rotatable drum.

Air bearing 300 includes housing 310. Housing 310, in one embodiment, is comprised of metal (e.g., aluminum, steel, etc.). Porous material 340 is dispose within housing 310. Housing 310 includes port 320 that receives pressurized air. The pressurized air is provided by a compressor (e.g., compressor 298) or a pressurized air tank. The pressurized air is provided at a constant pressure. The pressurized air is directed into area 330 within housing 310. The pressurized air is then forced through the pores of porous material 340. The pressurized air exiting the pores of the porous material (at the constant pressure) and forms an air gap 350 between the air bearing 300 and surface 360. Surface 360, in one embodiment, is a surface that faces the axial air bearings, such as surface 231 or surface 241. Surface 360, in one embodiment, is a convex surface that faces the radial air bearings, such as surface 224 or surface 226. In such an embodiment, housing 310 and porous material 340 include a convex surface that faces the convex surface 360.

Figure 4:
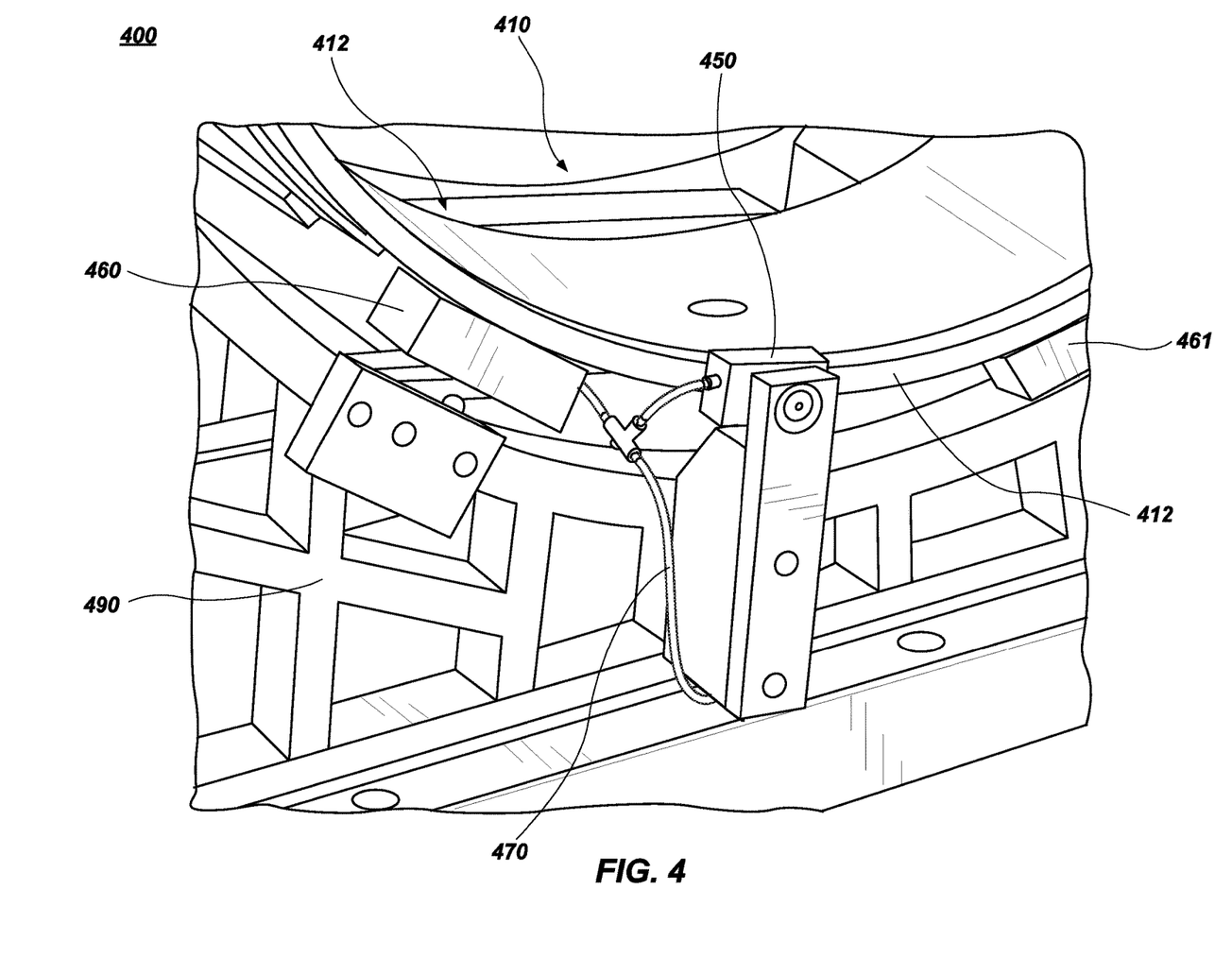
FIG. 4 is a cut-away perspective view of air bearings in a CT scanning system according to some embodiments.

FIG. 4 illustrates an embodiment of CT scanning system 400. CT scanning system 400 is similar to CT scanning system 200, as described herein. CT scanning system 400 includes rotatable drum 410 and cradle 490. Rotatable drum 410 may levitate during operation via radial air bearings 460 and 461 and axial air bearing 450. It should be appreciated that CT scanning system 400 includes additional radial and axial air bearing (not shown) on an opposite end of rotatable drum.

Radial air bearings 460 and 461 are disposed about 90 degrees with respect to each other. It should be appreciated that radial air bearings can be disposed at various degrees with respect to each other. For example, CT scanning system 400 may include two or more radial air bearings along distal end 412, where the radial air bearings are disposed approximately 30 degrees from one another.

CT scanning system 400 includes axial air bearing 450. CT scanning system 400 may include one or more axial air bearings proximate distal end 412. Likewise, CT scanning system 400 can include one or more opposing axial air bearings proximate an opposite distal end.

CT scanning system 400 includes hose 470. The pressurized air is directed to the respective air bearings via hose 470 from a compressor or air pump.

Figure 5A:
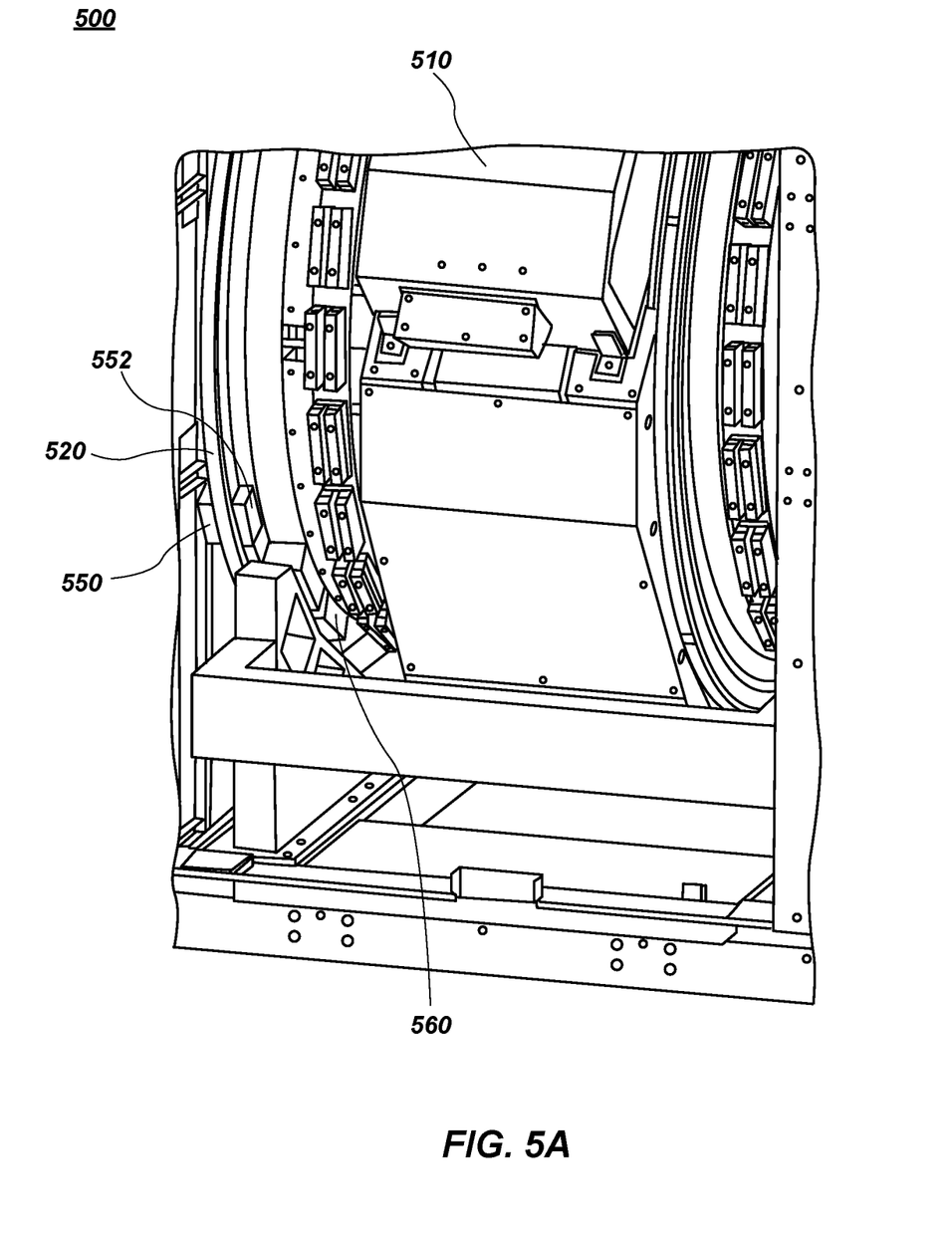
FIG. 5A is a cut-away perspective view of air bearings in a CT scanning system according to some embodiments.

FIG. 5A illustrates an embodiment of CT scanning system 500. CT scanning system 500, in various embodiments, is similar to CT scanning system 200 and 300. CT scanning system 500 includes rotatable drum 510. Drum 510 includes annular flange 520. Annular flange 520, in various embodiments, is similar to flange 220 or flange 222.

CT scanning system 500 includes radial air bearings 560 that are similar to at least radial air bearings 260. CT scanning system 500 also includes axial air bearings 550 and 552 that oppose one another. Axial air bearing 550 faces a first surface of flange 520 and axial air bearing 552 faces a second opposing face of flange 520. As such, axial air bearing 550 and axial air bearing 552 direct air flow in directions opposite from another. In various embodiments, flange 520 is disposed at either distal end of rotatable drum. Alternatively, flange 520 may be disposed at any location (e.g., middle) along the length of drum 510.

Figure 5B:
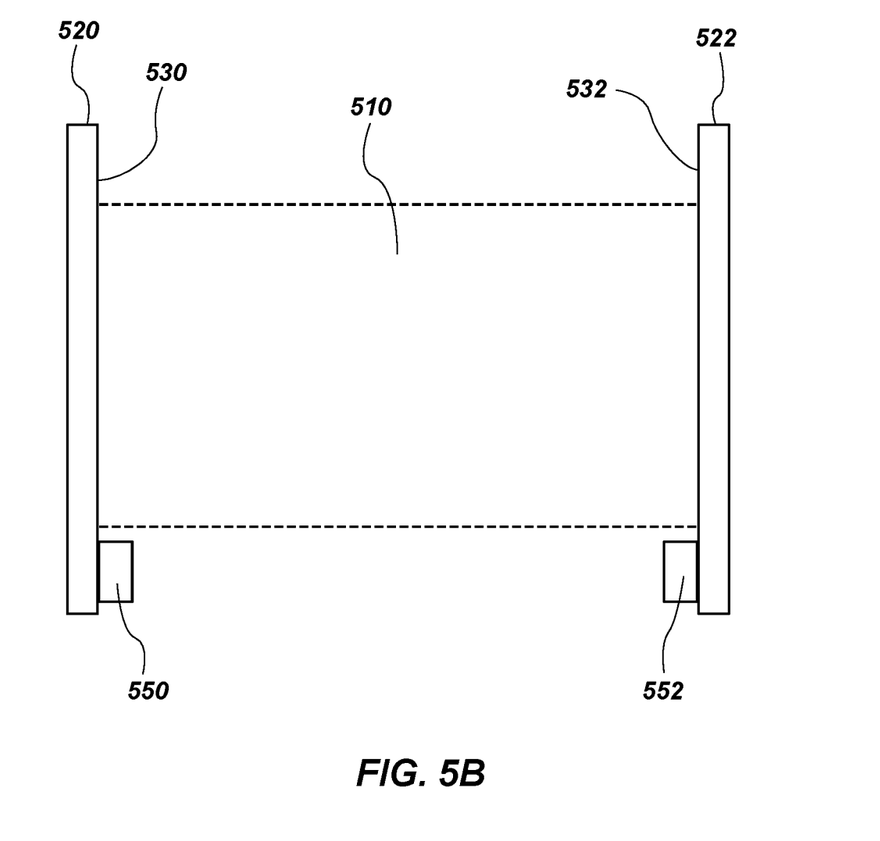
FIG. 5B is a side perspective view of air bearings in a CT scanning system according to some embodiments.

FIG. 5B illustrates an embodiment of CT scanning system 500. In the depicted embodiment, axial air bearings 550 and 552 oppose one another. Axial air bearing 550 is disposed proximate surface 530 of flange 520. In particular, axial air bearing 550 creates an air gap between the axial air bearing and surface 530. Similarly, axial air bearing 552 is disposed proximate surface 532 of flange 522. In particular, axial air bearing 552 creates an air gap between the axial air bearing and surface 532. As such, axial air bearings 550 and 552 direct air opposite one another.

Figure 6:
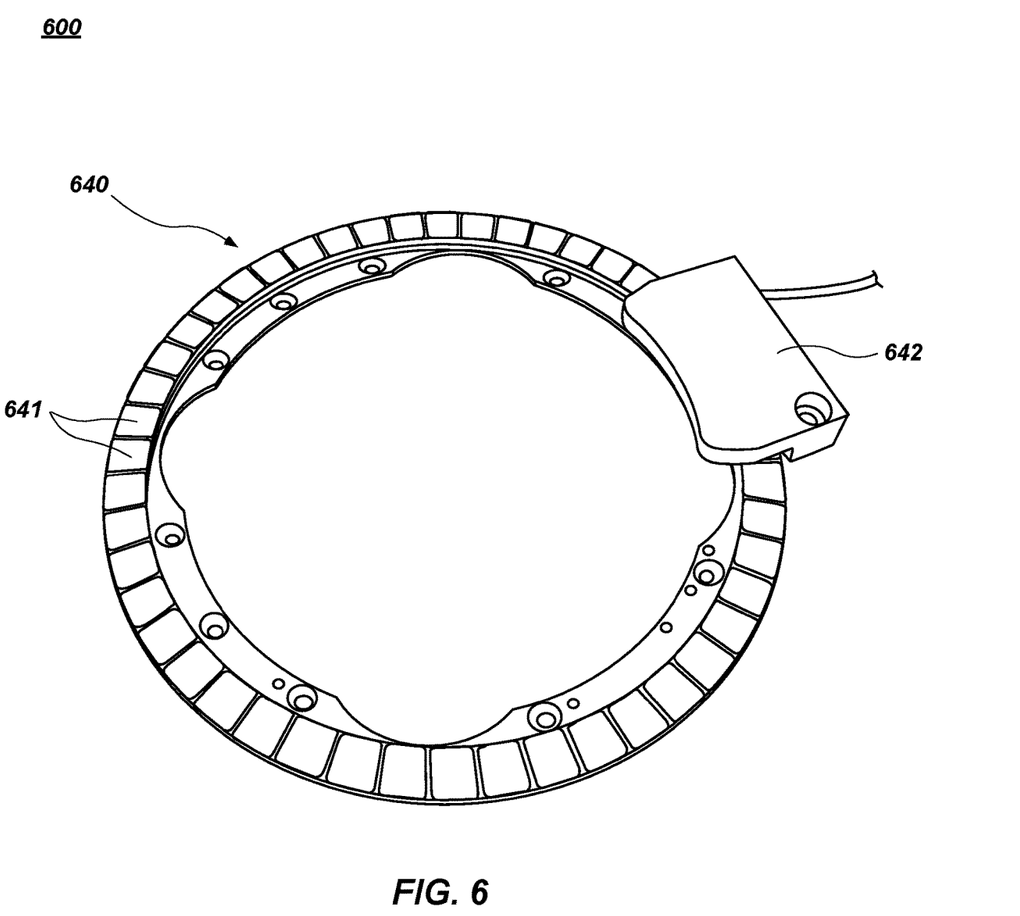
FIG. 6 is a perspective view of a linear induction motor according to some embodiments.

FIG. 6 illustrates an embodiment of induction motor 600 (e.g., linear arc motor). Motor 600 includes rotor 640 (e.g., rotor 240 in FIG. 2B) and stator 642 (e.g., stator 242 in FIG. 2B). Rotor 640 forms a ring shape. Rotor 640 is proximate a distal end of a rotatable drum. For example, referring to FIGS. 2A and 2B, rotor 640 is attached flange 222.

Rotor 640 includes an array of magnets 641. Magnets 641 are disposed proximate one another to form the ring shape of the rotor.

Stator 642, in one embodiment, is proximate a cradle that cradles the rotatable drum. For example, referring to FIGS. 2A and 2B, stator 642 (e.g., stator 242) is attached cradle 290. To drive the rotation of the rotatable drum, a current (e.g., alternating current (AC)) is driven to stator 642. For example, a motor driver (not shown) is a current source that drives the AC current to stator 642. Stator 642 includes coils (not shown) that generates changing magnetic fields in response to receiving the AC current. The changing magnetic fields induces a force on magnets 641 that causes rotor 640 to rotate about its axis. It is noted that rotor 640 and stator 642 do not physically contact one another during rest or during operation. As such, the rotatable drum (connected to rotor 640) is contactlessly rotated via motor 600.

In various embodiments, the magnetic field generated by motor 600 generates an axial force on the rotatable drum. For example, motor 600 induces an axial movement of the rotatable drum towards motor 600. The axial force of the motor 600 is opposed by a force generated by an opposing axial air bearing. For example, axial air bearings 252 generate a force that opposes the axial force generated by motor 600.

As described herein, during operation of a CT scanning system, the rotatable drum levitates via axial and radial air bearings. As such, the drum may rotate without generating any frictional forces. In one embodiment, motor 600 generates the requisite force to overcome inertia of the rotatable drum based, in part, on the lack of frictional forces to overcome. In one embodiment, motor 600 rotates the rotatable drum at approximately 225 RPM. It should be appreciated that motor 600 rotates the drum less than or greater than 225 RPM.

Figure 7A:
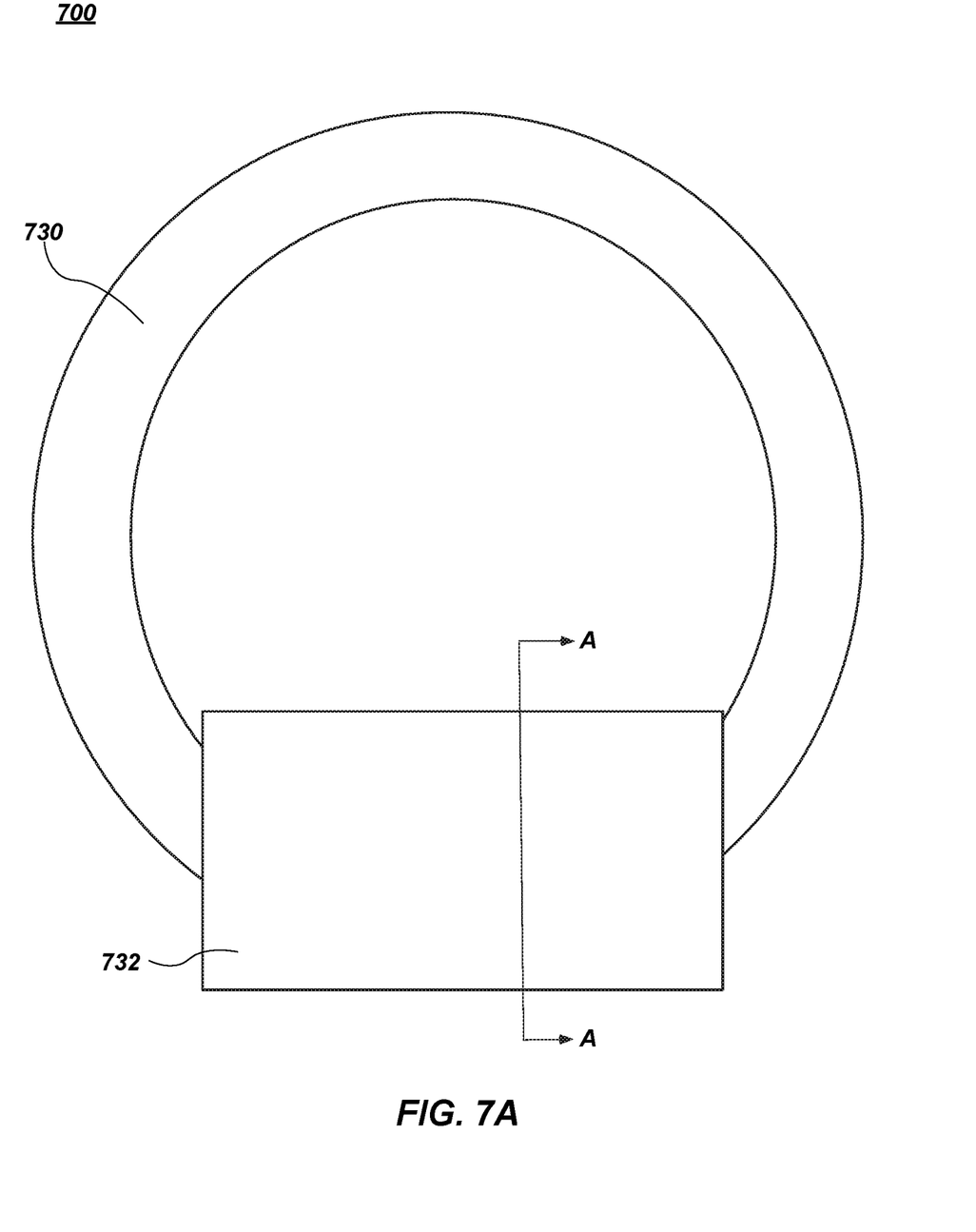
FIGS. 7A and 7B illustrate a contactless data-link according to some embodiments.

FIG. 7A illustrates an embodiment of a contactless data-link 700 (which also may be characterized as a contactless information transmission system). Data-link 700 includes rotor 730 and stator 732. Rotor 730 forms a ring shape. Rotor 730 is proximate a distal end of a rotatable drum. For example, referring to FIGS. 2A and 2B, rotor 730 is attached flange 220. In one embodiment, rotor 730 is embedded in flange 220. In another embodiment, rotor 730 is flange 220.

Stator 732, in one embodiment, is proximate a cradle that cradles the rotatable drum. For example, referring to FIGS. 2A and 2B, stator 732 is attached cradle 290.

In various embodiments, data-link 700 generates a magnetic field that induces an axial force on the rotatable drum. For example, data-link 700 induces an axial movement of the rotatable drum towards data-link 700. The axial force of the data-link 700 is opposed by a force generated by an opposing axial air bearing. For example, axial air bearings 250 generate a force that opposes the axial force generated by data-link 700.

Figure 7B:
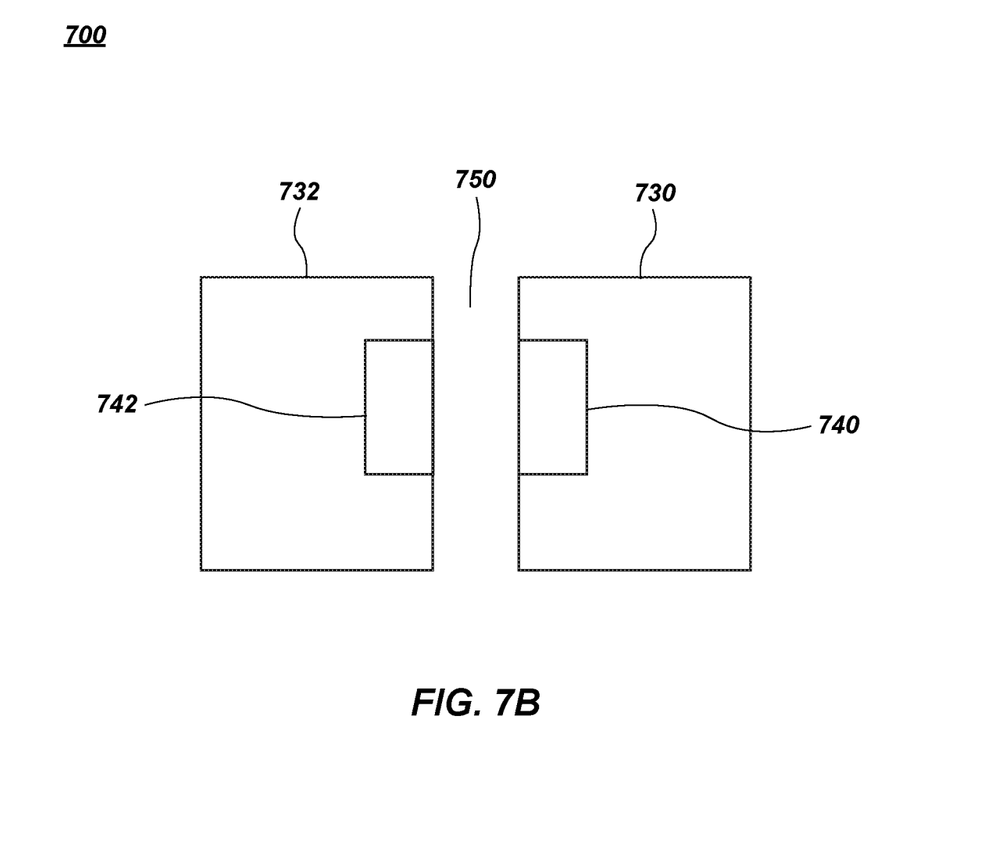

FIG. 7B illustrates a cross-sectional view of contactless data-link 700 along line A-A. Contactless data-link 700 includes a first antenna 740 proximate to a rotor 730 (e.g., 104 in FIG. 1; 230 in FIG. 2A) and a second antenna 742 proximate to stator 732 (e.g., 110 in FIG. 1; 232 in FIG. 2A).

Rotor 730 is typically separated from stator 732 by an air gap 750 that is defined by a space between the rotor 730 and stator 732 and is configured to enable rotation of the rotor 730 relative to stator 732. Typically, the first antenna 740 is mounted on rotor 730 within and/or adjacent the air gap 750 and the second antenna 742 is mounted on stator 732 within and/or adjacent the air gap 750, although other arrangements are contemplated. As such, the second antenna 742 may detect electromagnetic waves generated via the first antenna 740 that are propagated through the air gap 750 and/or the first antenna 740 may detect electromagnetic waves generated via the second antenna 742 that are propagated through the air gap.

Respective antennas 740 and 742 may be comprised of one or more physical channels respectively configured to convey information between rotor 730 and stator 732. Moreover, as may be described in more detail below, a transceiver (s) may be configured create two or more logical channels via a physical channel (e.g., by logically sub-dividing the physical channel into two or more logical channels). In this way, two or more types of information (e.g., respectively represented by different signals) may be transferred in a single direction and/or information may be transferred bi-directionally via a single physical channel, for example. By way of example and not limitation, in one embodiment, the contactless data-link comprises merely (e.g., exactly) one physical channel (e.g., one wire or other physical transmission medium), which a transceiver(s) may utilize to create two or more logical channels.

Although the foregoing cross-sectional view describes radial air gap 750 (e.g., between the entirety of the outer circumference of rotor 730 and the entirety of the inner circumference of stator 732), it may be appreciated that air gap 750, first antenna 740, and/or second antenna 742 may be arranged differently than the example arrangement. For example, in another embodiment, air gap 750 may be planar. In one embodiment, rotor 730 and stator 732 face one another. In another embodiment, rotor 730 and stator 732 are concentric to one another.

It may be appreciated that although reference is made herein to the communication system being comprised of first and second transceivers, respective transceiver may not perform both the functions of a receiver and a transmitter. For example, the first transceiver may function merely as a transmitter configured to transmit information across the contactless data-link and the second transceiver may function merely as a receiver configured to receive information transmitted across the contactless data-link and/or vice-versa. In another embodiment, the first transceiver and/or the second transceiver may behave in the tradition sense where the transceiver(s) is configured for both sending and receiving information. Thus, as provided herein, where a transceiver is illustrated and/or described, the transceiver may merely be a receiver or a transmitter. Similarly, where a transmitter or receiver is illustrated and/or described herein, such a transmitter or receiver may comprise a transceiver configured for both transmission and reception.

Referring to FIG. 1, image reconstructor 124 is configured to receive the projection space data that is output by the data acquisition component 122 (e.g., or output from the communication system). Image reconstructor 124 is also configured to generate image space data from the projection space data using a suitable analytical, iterative, and/or other reconstruction technique (e.g., back projection reconstruction, tomosynthesis reconstruction, iterative reconstruction, etc.). In this way, the data is converted from projection space to image space, a domain that may be more understandable by user 130 viewing the image(s), for example.

As used herein, data or information representative of an object may be referred to herein as imaging data. That is, imaging data may be used to generically refer to data or information in the projection space domain and/or in the image space domain that is representative of an object presently under examination and/or that previously underwent an examination.

Environment 100 also includes terminal 126, or workstation (e.g., a computer), configured to receive the image(s), which can be displayed on monitor 128 to user 130 (e.g., security personnel, medical personnel, etc.). In this way, user 130 can inspect the image(s) to identify areas of interest within object(s) 102. Terminal 126 can also be configured to receive user input which can direct operations of object examination apparatus 108 (e.g., a speed to rotate, a speed of a conveyor belt, etc.).

In environment 100, controller 132 is operably coupled to terminal 126. In one example, controller 132 is configured to receive input from terminal 126, such as user input for example, and to generate instructions for object examination apparatus 108 indicative of operations to be performed. For example, user 130 may desire to reexamine object(s) 102 at a different energy level, and controller 132 may issue a command instructing support article 112 to reverse direction (e.g., bringing object(s) 102 back into examination region 114 of object examination apparatus 108).

In one embodiment, the transceiver may be configured to create at least two logical channels for the transmission of information over a physical channel of the contactless data-link. A first logical channel may be utilized for transmitting a first type of information in a first direction and a second logical channel may be utilized for transmitting the first type of information in second direction and/or for transmitting a second type of information in the second direction and/or in the first direction. In this way, one or more types of information may be transmitted bi-directionally over the contactless data-link and/or two or more different types of information may be transmitted over the contactless data-link in a same and/or different direction. Types of information transmitted over the contactless data-link may include, among other things, imaging data, control data, and/or timing information. In some embodiments, the contactless data-link may be configured to support the transfer of information in merely an analog domain or in merely a digital domain, and the transceiver may be further configured to convert information between the analog and digital domains to facilitate transmission over the contactless data-link, for example.

To create the at least two logical channels for transmission of information over a physical channel, the transceiver may comprise a multiplexer and/or a demultiplexer. Such a multiplexer/demultiplexer may utilize multiplexing techniques, such as frequency-division multiplexing, time-division multiplexing, and/or code-division multiplexing, for example, to create the at least two logical channels.

Figure 8:
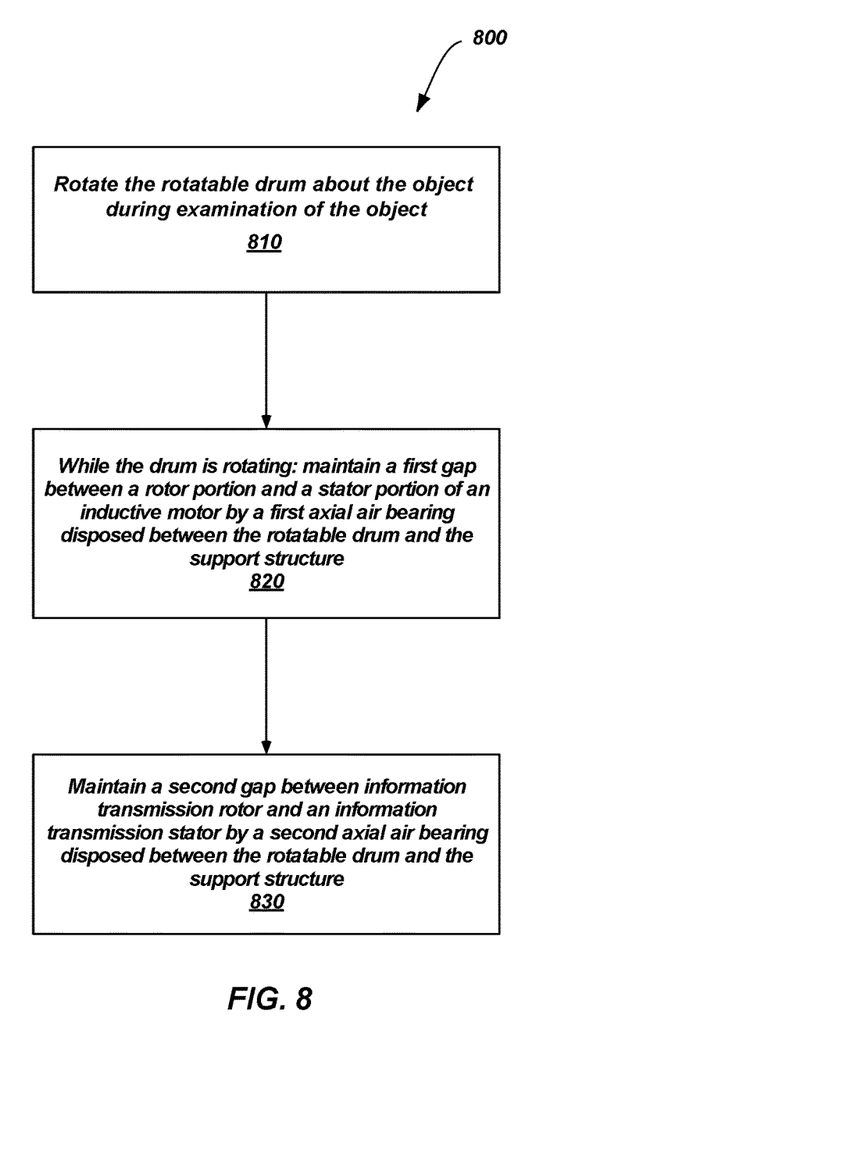
FIG. 8 is a flow chart of a method for examining an object by a CT scanner according to some embodiments.

FIG. 8 illustrates a method 800 for examining an object by a CT scanner according to some embodiments. At 810 of method 800, the rotatable drum is rotated about the object during examination of the object. For example, a contactless induction motor (e.g., motor 600) drives the rotation of a rotatable drum (e.g., rotatable drum 210) during an examination of an object (e.g., object 102) of the CT scanner.

At 820, while the drum is rotating, a first gap between a rotor portion and a stator portion of an inductive motor is maintained by a first axial air bearing disposed between the rotatable drum and the support structure. For example, axial air bearings 250 and 252 create an air gap between the respective axial air bearings and the rotatable drum. This constant air gap maintains axial alignment of the rotatable drum during operation. In particular, the constant air gap of the axial air bearings causes the air gap between the motor rotor (e.g., rotor 640) and motor stator 642.

At 830, a second gap is maintained between information transmission rotor and an information transmission stator by a second axial air bearing disposed between the rotatable drum and the support structure. For example, axial air bearings 250 and 252 create an air gap between the respective axial air bearings and the rotatable drum. This constant air gap maintains axial alignment of the rotatable drum during operation. In particular, the constant air gap of the axial air bearings causes the air gap between the information transmission rotor (e.g., rotor 640) and information transmission stator 732.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or." In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used, such terms are intended to be inclusive in a manner similar to the term "comprising." The claimed subject matter may be implemented as a method, apparatus, or article of manufacture (e.g., as software, firmware, hardware, or any combination thereof).

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B" or two different (or two identical) channels or the same channel).

Although the disclosure has been shown and described with respect to one or more implementations, equivalent alterations and modifications will occur to others skilled in the art based upon a reading and understanding of this specification and the accompanying drawings. The disclosure includes all such modifications and alterations and is limited only by the scope of the following claims and the legal equivalents thereof. In particular regard to the various functions performed by the above-described components (e.g., elements, resources, etc.), the terms used to describe such components are intended to correspond, unless otherwise indicated, to any component that performs the specified function (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. An assembly for a CT system, comprising:
   a rotatable drum defining a bore and configured for rotation about an object positioned within the bore;
   a support structure configured to support the rotatable drum during a rotation of the rotatable drum;
   a first radial air bearing disposed between the rotatable drum and the support structure and positioned proximate to a first distal end of the rotatable drum, the first radial air bearing oriented toward a first radial surface of the rotatable drum located radially and longitudinally inward from a first annular flange at the first distal end of the rotatable drum; and
   a second radial air bearing disposed between the rotatable drum and the support structure and positioned proximate to a second, opposite distal end of the rotatable drum, the second radial air bearing oriented toward a second radial surface of the rotatable drum located radially and longitudinally inward from a second annular flange at the second distal end of the rotatable drum, wherein the first radial air bearing and the second radial air bearing are located at different longitudinal positions along a longitudinal axis of the rotatable drum, and wherein the first radial air bearing and the second radial air bearing are configured to levitate the rotatable drum relative to the support structure.

2. The assembly for the CT system of claim 1, further comprising:
   an induction motor configured to rotate the rotatable drum, the induction motor comprising a stator portion and a rotor portion, wherein the rotor portion is configured to move relative to the stator portion while the induction motor is rotating the rotatable drum.

3. The assembly for the CT system of claim 2, further comprising:
   an information transmission rotor; and
   an information transmission stator, wherein the information transmission rotor is configured to move relative to the information transmission stator while the induction motor is rotating the rotatable drum.

4. The assembly for the CT system of claim 1, wherein the support structure only partially circumferentially surrounds the rotatable drum.

5. The assembly for the CT system of claim 1, further comprising:
   a radiation source operably coupled to the rotatable drum; and
   a radiation detector operably coupled to the rotatable drum.

6. The assembly for the CT system of claim 1, further comprising:
   a third radial air bearing disposed between the rotatable drum and the support structure and disposed proximate the first distal end of the rotatable drum; and
   a fourth radial air bearing disposed between the rotatable drum and the support structure and positioned proximate the second distal end of the rotatable drum, wherein the third radial air bearing and the fourth radial air bearing are spaced apart from one another relative to a longitudinal axis of the rotatable drum, and wherein the third radial air bearing and the fourth radial air bearing are configured to levitate the rotatable drum relative to the support structure.

7. The assembly for the CT system of claim 1, further comprising:
   a first axial air bearing disposed between the rotatable drum and the support structure; and
   a second axial air bearing opposite the first axial air bearing and disposed between the rotatable drum and the support structure, wherein the first axial air bearing and the second axial air bearing are configured to cooperatively maintain axial alignment of the rotatable drum relative to the support structure.

8. The assembly for the CT system of claim 7, wherein the first axial air bearing is disposed proximate the first distal end and the second axial air bearing is disposed proximate to the second distal end.

9. The assembly for the CT system of claim 7, wherein the first axial air bearing and the second axial air bearing are disposed proximate one of the first distal end and the second distal end.

10. The assembly for the CT system of claim 7, wherein the first axial air bearing and the second axial air bearing direct air flow away from each other.

11. The assembly for the CT system of claim 7, wherein the first axial air bearing and the second axial air bearing are configured to direct air flow towards each other when a portion of the rotatable drum is located between the first and second axial air bearings.

12. The assembly for the CT system of claim 7,
wherein one of the first axial air bearing and the second axial air bearing is configured to direct air flow on a first surface of the first annular flange.

13. The assembly for the CT system of claim 12, wherein the other of the first axial air bearing and the second axial air bearing is configured to direct air on a second surface of the first annular flange.

14. The assembly for the CT system of claim 12,
wherein the other of the first axial air bearing and the second axial air bearing is configured to direct air flow on a surface of the second annular flange.

15. Performing an examination of an object using an imaging system of claim 1.

16. An assembly for a CT system, comprising:
a rotatable drum defining a bore and configured for rotation about an object positioned within the bore, the rotatable drum comprising a first annular flange at a first distal end of the rotatable drum and a second annular flange at a second distal end of the rotatable drum;
a support structure configured to support the rotatable drum during a rotation of the rotatable drum;
a first axial air bearing disposed between the rotatable drum and the support structure and positioned proximate to the first distal end of the rotatable drum, the first axial air bearing oriented toward a first at least substantially planar surface of a first annular flange at the first distal end of the rotatable drum;
a second axial air bearing disposed between the rotatable drum and the support structure and positioned proximate to the first distal end of the rotatable drum, the second axial air bearing oriented toward a second at least substantially planar surface of the first annular flange at the first distal end of the rotatable drum, the first at least substantially planar surface being located on a side of the first annular flange opposite the second
at least a linear motor comprising a rotor portion proximate to the first annular flange; and
an information transmission rotor proximate to the second annular flange.

17. The assembly for the CT system of claim 16, wherein the linear motor further comprises a stator portion disposed between the support structure and the rotatable drum.

18. The assembly for the CT system of claim 16, wherein the rotor portion of the linear motor is attached to a surface of the first annular flange opposite the rotatable drum.

19. The assembly for the CT system of claim 16, further comprising:
an information transmission stator disposed between the support structure and the rotatable drum.

20. The assembly for the CT system of claim 16, wherein the information transmission rotor is attached to a surface of the second annular flange opposite the rotatable drum.

21. The assembly for the CT system of claim 16, wherein a diameter of the first annular flange is larger than a diameter of the rotatable drum at the first distal end and a diameter of the second annular flange is larger than a diameter of the rotatable drum at the second distal end.

22. The assembly for the CT system of claim 16, further comprising:
a first radial air bearing; and
a second radial air bearing, wherein the first radial air bearing and the second radial air bearing are spaced apart from one another relative to a longitudinal axis of the rotatable drum.

23. The assembly for the CT system of claim 16, further comprising:
a radiation source operably coupled to the rotatable drum; and
a radiation detector operably coupled to the rotatable drum.

24. The assembly for the CT system of claim 16, wherein one of the first axial air bearing and the second axial air bearing is configured to oppose a magnetic force generated by the information transmission rotor and the other of the first axial air bearing and the second axial air bearing is configured to oppose a magnetic force generated by the rotor portion of the linear motor.

25. Performing an examination of an object using an imaging system of claim 16.

26. A method for examining an object by a CT scanner, comprising:
rotating a rotatable drum about the object during examination of the object; and
while the rotatable drum is rotating:
maintaining a first gap between a rotor portion and a stator portion of an inductive motor by a first axial air bearing disposed between the rotatable drum and a support structure, the first axial air bearing oriented toward a first at least substantially planar surface of a first annular flange at a first distal end of the rotatable drum; and
maintaining a second gap between information transmission rotor and an information transmission stator by a second axial air bearing disposed between the rotatable drum and the support structure, the second axial air bearing oriented toward a second at least substantially planar surface of a second annular flange at a second, opposite distal end of the rotatable drum.

27. The method of claim 26, further comprising placing the object in a bore of the rotatable drum.

* * * * *

UNITED STATES PATENT AND TRADEMARK OFFICE
CERTIFICATE OF CORRECTION

| | | |
|---|---|---|
| PATENT NO. | : 10,918,345 B2 | Page 1 of 1 |
| APPLICATION NO. | : 16/507555 | |
| DATED | : February 16, 2021 | |
| INVENTOR(S) | : Jeffrey Knox | |

It is certified that error appears in the above-identified patent and that said Letters Patent is hereby corrected as shown below:

In the Claims

Claim 16, Column 13, Line 41, change "at least a linear motor" to --at least substantially planar surface; a linear motor--

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*